US006713410B1

(12) United States Patent
Perring et al.

(10) Patent No.: US 6,713,410 B1
(45) Date of Patent: Mar. 30, 2004

(54) METHOD FOR TEXTILE TREATMENT FOR SPANDEX CONTAINING FABRICS

(75) Inventors: Keith Douglas Perring, Kent (GB); Christopher Francis Clements, Kent (GB); Angus Peter MacMaster, Kent (GB); Raymond Palmen, Vessy (CH); Olivier William John, Geneva (CH)

(73) Assignee: E.I. du Pont de Nemours and Co., Wilmington, DE (US)

( * ) Notice: Subject to any disclaimer, the term of this patent is extended or adjusted under 35 U.S.C. 154(b) by 0 days.

(21) Appl. No.: 09/509,863

(22) PCT Filed: Oct. 9, 1998

(86) PCT No.: PCT/GB98/03056

§ 371 (c)(1),
(2), (4) Date: Jul. 14, 2000

(87) PCT Pub. No.: WO99/19553

PCT Pub. Date: Apr. 22, 1999

(30) Foreign Application Priority Data

Oct. 10, 1997 (GB) ............................................ 9721588

(51) Int. Cl.[7] ......................... B32B 27/04; B32B 27/12; B32B 5/02; D03D 15/08; D04H 1/00; D04H 13/00; A61K 7/46

(52) U.S. Cl. ......................... 442/96; 442/184; 442/329; 8/115.56; 512/1

(58) Field of Search .......................... 442/96, 184, 329; 8/115.56, 115.7; 512/1

(56) References Cited

U.S. PATENT DOCUMENTS

| | | | | | |
|---|---|---|---|---|---|
| 4,134,838 | A | | 1/1979 | Hooper et al. | 252/8.8 |
| 4,278,658 | A | | 7/1981 | Hooper et al. | 424/65 |
| 4,288,341 | A | | 9/1981 | Hooper et al. | 252/107 |
| 4,289,641 | A | | 9/1981 | Hooper et al. | 252/96 |
| 4,304,679 | A | | 12/1981 | Hooper et al. | 252/106 |
| 4,844,902 | A | * | 7/1989 | Grohe | 424/449 |
| 4,882,220 | A | * | 11/1989 | Ono et al. | 428/240 |
| 5,000,899 | A | | 3/1991 | Dreibelbis et al. | 264/205 |
| 5,008,517 | A | * | 4/1991 | Brekkestran et al. | 219/211 |
| 5,288,779 | A | | 2/1994 | Goodrich | 524/121 |
| 5,362,432 | A | | 11/1994 | Houser et al. | 264/205 |
| 5,482,635 | A | | 1/1996 | Behan et al. | 252/8.6 |
| 5,554,588 | A | | 9/1996 | Behan et al. | 512/1 |
| 6,465,420 | B1 | * | 10/2002 | Perring et al. | 512/1 |

FOREIGN PATENT DOCUMENTS

| | | | | |
|---|---|---|---|---|
| EP | 0 003 172 | | 10/1979 | A61K/7/32 |
| EP | 0 581 274 A | | 2/1994 | D06M/23/12 |
| EP | 0 841 391 A | | 5/1998 | C11D/3/50 |
| GB | 1 596 792 | | 8/1981 | A61L/9/01 |
| JP | 05295667 A | * | 11/1993 | D06M/23/12 |
| WO | 93/14259 A | | 7/1993 | D06M/11/75 |

OTHER PUBLICATIONS

Translation to JP 05–295667 A to Ono et al.*
Database WPI, Section CH, Week 8949, Derwent Publications Ltd., London, GB; AN 89–361939—XP002090301 & JP 01 272875A (KANEBO Ltd), Oct. 31, 1989.
Database WPI, Section CH, Week 9426, Derwent Publications Ltd., London, GB; AN 94–211413—XP002090302 & JP 06 146112 A (NISSHINBO Ind Inc), May 27, 1994.

* cited by examiner

*Primary Examiner*—Elizabeth M. Cole
*Assistant Examiner*—Jeremy Pierce
(74) *Attorney, Agent, or Firm*—George A. Frank

(57) ABSTRACT

A method of treating textile which is yarn or fabric containing spandex fibres, comprising contracting the textile with a perfume so that the perfume is deposited on the fabric. The perfume contains a mixture of fragrance materials which preferentially deposit on the spandex fibres. The yarn of fabric may be made up into garments.

11 Claims, No Drawings

METHOD FOR TEXTILE TREATMENT FOR SPANDEX CONTAINING FABRICS

This invention relates to the treatment of textiles containing spandex fibres.

At the present time, many garments are made from fabric which contains a mixture of fibres, a proportion of which are elastic, so that the fabric has the ability to stretch and to recover from stretch. Spandex fibres are commonly used for this purpose. The term "Spandex" has been adopted as a generic term by the United States Federal Trade Commission to denote a manufactured fibre in which the fibre-forming substance is a long chain synthetic polymer composed of at least 85% of a segmented polyurethane. A discussion of such fibres can be found in "History of Spandex Elastomeric Fibres" by A. J. Ultee, which is a chapter starting at page 278 in Man-Made Fibres: Their Origin and Development, edited by R. V. Seymour and R. S. Porter, Elsevier 1993. Spandex fibres are also referred to as "elastane" or "elasthane" fibres.

Another discussion of such fibres is found under the heading "Segmented Polyurethanes" at page 613 of Handbook of Textile Fibres by J. Gordon Cook, 5th Ed. Merrow Publishing Company 1984. Further description of elastanes and their applications can be found in "Synthesefasern: Grundlagen, Technologie, Verarbeitung und Anwendung", B von Falkei (editor), Verlag Chemie (1981). Commercially available elastanes are well known, in particular as sold under the name LYCRA®, a registered trade mark of DuPont de Nemours and Company. Patents relating to such fibres include U.S. Pat. No. 5,000,899, U.S. Pat. No. 5,288,779 and U.S. Pat. No. 5,362,432.

The deposition of perfume onto garments and other fabrics during laundering has been established for many years. Perfume is incorporated into laundry products such as detergent compositions for fabric washing and rinse conditioners for softening the fabrics.

Although the perfume serves to cover the base odour of such a product and to give the unused product an attractive fragrance, it also deposits on the fabric.

Certain perfumes have the ability to provide deodorant action against body odour, either when directly applied to human skin, or when included in a laundry product. Such perfumes are described in EP-B-3172, U.S. Pat. No. 4,304,679, U.S. Pat. No. 4,278,658, U.S. Pat. No. 4,134,838, U.S. Pat. No. 4,268,341 and U.S. Pat. No. 4,289,641, U.S. Pat. No. 5,482,635 and U.S. Pat. No. 5,554,588.

SUMMARY OF THE INVENTION

We have now found that a number of fragrance materials used in perfumery are able to deposit and then be retained better on spandex fibres than on a number of other textile fibres.

Delivery of fragrance materials to fabric can take place during washing, as is well known. The present invention appreciates that the application of perfume to textiles containing spandex fibres can be utilised in the treatment of textiles which are newly made—that is to say textile goods which have never been worn as garments by a consumer.

Therefore in one aspect the present invention provides a method of treating textile which is yarn or fabric containing spandex fibres, comprising contacting the textile with a perfume so that the perfume is deposited on the fabric. Preferably, the fabric is unworn. It may have been made up into a garment.

In a related second aspect, the invention provides textile which is yarn or fabric containing spandex fibres, having perfume deposited on the textile. Preferably, the fabric is unworn. It may have been made up into a garment.

We have observed that a range of fragrance materials deposited on such textiles will still be perceptible on the fabric, even after several washes of the fabric using laundry products with a different perfume, or none.

The invention also provides use of a perfume composition in the treatment of textile which is yarn or fabric containing spandex and other fibres, to deposit fragrance materials at a greater concentration on the spandex fibres than on the other fibres. Preferably, the fabric is unworn.

In significant forms of this invention, the perfume used to treat the textile (or the combination of fragrance materials deposited thereon) is a deodorant perfume. Then when the textile is made into a garment, that garment will have an in-built deodorant property.

DETAILED DESCRIPTION

The various aspects of this invention, preferred forms and materials useful therein will now be discussed in greater detail.

Textiles

The textiles to which this invention relates include spandex fibres. As mentioned earlier, this term denotes a manufactured fibre in which the fibre forming substance is a long chain synthetic polymer compound composed of at least 85% of a segmented polyurethane.

Thus the polymer which is spun into spandex fibres is a copolymer incorporating urethane linkages. Generally the polymer contains so-called soft (i.e. lower melting) segments which may be polyalkylene ethers or polyesters and so-called hard (i.e. higher melting) segments which are portions derived from the reaction of an isocyanate and a chain extender which is typically a diamine.

The soft segments may be poly(tetramethylene)ethers, possibly containing substituted tetramethylene glycol residues as described in U.S. Pat. No. 5,000,899. Organic diisocyanates which may be used include conventional diisocyanates, such as diphenylmethane-4,4'-diisocyanate, also known as methylene-bis(4-phenylisocyanate) or "MDI", 2,4-tolylene diisocyanate, methylene-bis(4-cyclohexylisocyanate), isophorone diisocyanate, tetramethylene-p-xylylene diisocyanate, and the like. MDI is preferred.

Chain extenders used in producing the hard segment of the fibres preferably include one or more of ethylenediamine (EDA), 1,3-propylenediamine, 1,4-cyclohexanediamine, hydrogenated m-phenylenediamine (HPMD), 2-methylpentamethylene diamine (MPMD) and 1,2-propylene diamine. More preferably, the chain extender is one or more of ethylenediamine, 1,3-propylenediamine, and 1,4-cyclohexanediamine, optionally mixed with HPMD, MPMD and/or 1,2-propylenediamine.

Spandex fibres with poly(tetramethylene) ethers as the soft segments are marketed by DuPont de Nemours International S.A. under the registered trade mark LYCRA® of DuPont de Nemours and Company.

Spandex fibres are generally mixed with other fibres such as cotton, polyamide, wool, polyester and acrylics and made into yarn which is then made into fabric. The content of spandex fibres is usually in a range from 0.5% by weight of the yarn or fabric up to 50%, more usually from 1 to 30% by weight of the yarn or fabric.

A wide range of garments may contain spandex fibres in the fabric, including active sports wear, intimate apparel, hosiery and a variety of ready to wear casual clothing.

The textiles which are treated with a perfume composition prior to wearing may be yarn which is later made into fabric, or may be fabric in the form of a web or lengths from a web which have not yet been made into garments, or may possibly be garments.

Preferably the treatment with a perfume composition is carried out while treating with other material in a conventional process step, especially a wet stage in which the yarn or fabric is treated with a finishing agent to improve its hand or appearance.

However, the perfume composition may be included directly into the spandex fibre. A fabric may be made using the spandex fibre alone. Alternatively, the spandex fibre may be covered or mixed with other fibres and made into a yarn which is then made into fabric.

The materials which may be applied to fabric in a conventional finishing treatment include resins to confer stiffness, fabric stability or permanent press, fabric softeners, flame retardants, fabric brighteners, anti-snag agents, materials to confer soil or stain resistance and water repellants.

Techniques which are conventionally used to apply such materials are padding and exhaustion, both well known in the technology of textile manufacture.

Treatment with a perfume composition in accordance with this invention can be carried out by including the perfume composition in the liquor used in a process as above.

The amount of perfume deposited on the fabric in a treatment step carried out on fabric will generally be from 0.001% to 1% by weight of the fabric.

Fragrance Materials

We have found that a range of fragrance materials deposit well on, or are retained well on, spandex fibres. Such materials include the following two categories:

Category A hydroxylic materials which are alcohols, phenols or salicylates, with an octanol/water partition coefficient (P) whose common logarithm ($log_{10}P$) is 2.5 or greater, and a gas chromatographic Kovats index (as determined on polydimethylsiloxane as non-polar stationary phase) of at least 1050.

Category B esters, ethers, nitriles, ketones or aldehydes, with an octanol/water partition coefficient (P) whose common logarithm ($log_{10}P$) is 2.5 or greater, and a gas chromatographic Kovats index (as determined on polydimethylsiloxane as non-polar stationary phase) of at least 1300.

The octanol-water partition coefficient (or its common-logarithm 'logP') is well known in the literature as an indicator of hydrophobicity and water solubility (see Hansch and Leo, Chemical Reviews, 71, 526–616, (1971); Hansch, Quinlan and Lawrence, J.Organic Chemistry, 33, 347–350 (1968). Where such values are not available in the literature they may be measured directly, or estimated approximately using mathematical algorithms. Software providing such estimations are available commercially, for example 'LogP' from Advanced Chemistry Design Inc.

A requirement for $log_{10}P$ of 2.5 or more calls for materials which are somewhat hydrophobic.

Kovats indices are calculated from the retention time in a gas chromatographic measurement referenced to the retention time for alkanes [see Kovats, Helv.Chim.Acta 41, 1915 (1958)]. Indices based on the use of a non-polar stationary phase have been used in the perfumery industry for some years as a descriptor relating to the molecular size and boiling point of ingredients. A review of Kovats indices in the perfume industry is given by T Shibamoto in "Capillary Gas Chromatography in Essential Oil Analysis", P Sandra and C Bicchi (editors), Huethig (1987), pages 259–274. A common non-polar phase which is suitable is 100% dimethyl polysiloxane, as supplied for example under a variety of tradenames such as RP-1 (Hewlett-Packard), CP Sil 5 CB (Chrompack), OV-1 (Ohio Valley) and Rtx-1 (Restek).

Materials of low Kovats index tend to be volatile and are not retained well on many fibres.

We have found that when perfumery materials have partition coefficient as above and a relatively high value of Kovats index, deposition and retention on spandex tends to be greater than on other fibres. Preferably therefore, the perfume composition contains at least 50 wt %, better at least 70 or 80 wt % of materials from the categories above.

We have found that there is a particularly high enhancement of deposition and retention on spandex, compared to other fibres, with materials within the above categories and having a Kovats index of not more than 1600. These sub-sets of categories A and B may be termed categories A' and B'. Preferably therefore, the perfume composition contains at least 10 wt %, better at least 20 wt % or 25 wt % of such materials. In some preferred perfumes the amount of fragrance materials from categories A' and B' is at least 40 wt % in total.

Such fragrance materials are of mid-range volatility (i.e. intermediate between the volatile perfume materials used as "top-notes" and the materials of low volatility which are customarily used as "base notes" in perfumes). These materials of mid-range volatility are often not perceptible on other fabrics such as cotton, polyamide and polyester after washing and drying.

Category A includes alcohols of general formula ROH where the hydroxyl group may be primary, secondary or tertiary, and the R group is an alkyl or alkenyl group, optionally branched or substituted, cyclic or acyclic, such that ROH has partition coefficient and Kovats properties as defined above. Alcohols of Kovats index 1050 to 1600 are typically monofunctional alkyl or arylalkyl alcohols with molecular weight falling within the range 150 to 230.

Category A also includes phenols of general formula ArOH, where the Ar group denotes a benzene ring which may be substituted with one or more alkyl or alkenyl groups, or with an ester grouping $—CO_2A$, where A is a hydrocarbon radical, in which case the compound is a salicylate. ArOH has partition coefficient and Kovats index as defined above. Typically, such phenols with Kovats index 1050 to 1600 are monohydroxylic phenols with molecular weight falling within the range 150 to 210.

A sub-set of fragrance materials which are particularly preferred are those with a partition coefficient of 1000 or more, i.e. $log_{10}P$ of 3 or more, and a Kovats parameter of 1100 up to 1600.

Some examples of hydroxylic ingredients which fulfil the above criteria for category A' are listed as a table below. Materials which are in the particularly preferred sub-set are marked with an asterisk. Semitrivial names are those used in standard texts known within the perfume industry, particularly: Common Fragrance and Flavor Materials by Bauer, Garbe and Surburg, VCH Publ., 2nd edition (1990), and Perfume and Flavour Materials, Steffen Arctander, published in two volumes by the author (1969).

| Examples of fragrance materials in category A' | |
|---|---|
| 1-(2'-tert-butylcyclohexyloxy)-butan-2-ol* | |
| 3-methyl-5-(2',2',3'-trimethylcyclopent-3-enyl)-pentan-2-ol* | |
| 4-methyl-3-decen-5-ol* | |
| amyl salicylate* | |
| 2-ethyl-4(2',2',3-trimethylcyclopent-3'-enyl)but-2-enol* | (Bangalol, TM) |
| borneol* | |
| carvacrol* | |
| citronellol* | |
| 9-decenol* | |
| dihydroeugenol* | |
| dihydrolinalol* | |
| dihydromyrcenol | |
| dihydroterpineol* | |
| eugenol | |
| geraniol* | |
| hydroxycitronellal* | |
| isoamyl salicylate* | |
| isobutyl salicylate* | |
| isoeugenol* | |
| linalol | |
| menthol* | |
| nerolidol* | |
| nerol* | |
| para tert-butyl cyclohexanol* | |
| phenoxanol* | |
| terpineol | |
| tetrahydrogeraniol* | |
| tetrahydrolinalol | |
| tetrahydromyrcenol | |
| thymol* | |
| 2-methoxy-4-methylphenol | (Ultravanil, TM) |
| (4-isopropylcyclohexyl)-methanol* | |

Some examples of fragrance materials which are in category A but which have Kovats index above 1600 (so as to fall outside category A') are:

benzyl salicylate cyclohexyl salicylate hexyl salicylate patchouli alcohol farnesol Category B is eaters, ketones, aldehydes, nitriles or ethers which have an octanol-water partition coefficient whose common logarithm ($\log_{10}P$) is at least 2.5, and a Kovats index of at least 1300 (non-polar phase).

Ingredients of Category B are of general formula RX, where X may be in a primary, secondary or tertiary position, and is one of the following groups: —COA, —OA, —$CO_2$A, —CN or —CHO. The groups R and A are hydrocarbon residues, cyclic or non-cyclic and optionally substituted. In some forms of this invention, category B excludes any material with a free hydroxy group, so that where a hydroxyl group is present, the material should be considered only for Category A membership. Typically, the materials of Category B with Kovats index not exceeding 1600 (which may be called category B') are monofunctional compounds with molecular weights in the range 160 to 230.

A sub-set of particularly preferred fragrance materials within category B' is those with a Kovats parameter falling within the range 1350 up to 1600, and possessing a molecular structure containing a ring, such as phenyl or cycloalkyl.

A number of fragrance materials which fulfil the above criteria for category B' are listed in the table below. Materials which are in the particularly preferred sub-set are marked with an asterisk.

| Examples of fragrance materials in category B' | |
|---|---|
| 1-methyl-4-(4-methyl-3-pentenyl)-3-cyclohexene-1-carbaldehyde* | |
| 1-(5', 5'-dimethylcyclohexenyl)-pent-en-1-one* | |
| 2-heptyl cyclopentanone* | |
| 2-methyl-3-(4'-tert-butylphenyl)propanal | |
| 2-methylundecanal | |
| 2-undecenal | |
| 2,2-dimethyl-3-(4'-ethylphenyl)-propanal | |
| 3-(4'-isopropylphenyl)-2-methylpropanal | |
| 4-methyl-4-phenylpent-2-yl acetate* | |
| allyl cyclohexyl propionate* | |
| allyl cyclohexyloxyacetate* | |
| amyl benzoate* | |
| methyl ethyl ketone trimers | (Azarbre, TM) |
| benzophenone* | |
| 3-(4'-tert-butylphenyl)-propanal | (Bourgeonal, TM) |
| caryophyllene | |
| cis-jasmone* | |
| citral diethyl acetal | |
| citronellal diethyl acetal | |
| citronellyl acetate | |
| phenylethyl butyl ether | (Cressanther, TM) |
| damascone, alpha-* | |
| damascone, beta-* | |
| damascone, delta-* | |
| decalactone, gamma-* | |
| dihydro isojasmonate* | |
| dihydrojasmone* | |
| dihydroterpinyl acetate | |
| dimethyl anthranilate* | |
| diphenyl oxide* | |
| diphenylmethane | |
| dodecanal | |
| dodecen-2-al | |
| dodecane nitrile | |
| 1-ethoxy-1-phenoxyethane | (Efetaal, TM) |
| 3-(1'-ethoxyethoxy)-3,7-dimethylocta-1,6-diene | (Elintaal Forte (TM) |
| 4-(4'-methylpent-3'-enyl)-cyclohex-3-enal | (Empetaal, TM) |
| ethyl tricyclo[5.2.1.0-2,6-]decane-2-carboxylate* | |
| 1-(7-isopropyl-5-methylbicyclo[2.2.2]oct-5-en-2-yl)-1-ethanone* | (Felvinone, TM) |
| allyl tricyclodecenyl ether* | (Fleuroxene, TM) |
| tricyclodecenyl propanoate* | (Florocyclene, TM) |
| gamma-undecalactone* | |
| n-methyl-n-phenyl-2-methylbutanamide* | (Gardamide, TM) |
| tricyclodecenyl isobutyrate* | (Gardocyclene, TM) |
| geranyl acetate | |
| hexyl benzoate* | |
| ionone alpha* | |
| ionone beta* | |
| isobutyl cinnamate* | |
| isobutyl quinoline* | |
| isoeugenyl acetate* | |
| 2,2,7,7-tetramethyltricycloudecan-5-one* | (Isolongifolanone, TM) |
| tricyclodecenyl acetate* | (Jasmacyclene, TM) |
| 2-hexylcyclopentanone | (Jasmatone, TM) |
| 4-acetoxy-3-pentyltetrahydropyran* | (Jasmopyrane TM) |
| ethyl 2-hexylacetoacetate | (Jessate, TM) |
| 8-isopropyl-6-methylbicyclo [2.2.2]oct-5-ene-2-carbaldehyde | (Maceal, TM) |
| methyl 4-isopropyl-1-methylbicyclo[2.2.2]oct-5-ene-2-carboxylate* | |
| methyl cinnamate | |
| aipha iso methyl ionone* | |
| methyl naphthyl ketone* | |
| nerolin | |
| nonalactone gamma | |
| nopyl acetate* | |
| para tert-butyl cyclohexyl acetate | |
| 4-isopropyl-1-methyl-2-[1'-propenyl]-benzene* | (Pelargene , TM) |
| phenoxyethyl isobutyrate* | |
| phenylethyl isoamyl ether* | |
| phenylethyl isobutyrate* | |
| tricyclodecenyl pivalate* | (Pivacyclene, TM) |

-continued

| Examples of fragrance materials in category B' | |
|---|---|
| phenylethyl pivalate* | (Pivarose, TM) |
| phenylacetaldehyde hexylene glycol acetal* | |
| 2,4-dimethyl-4-phenyltetrahydrofuran | (Rhubafuran, TM) |
| rose acetone* | |
| terpinyl acetate | |
| 4-isopropyl-1-methyl-2-[1'-propenyl]-benzene | (Verdoracine, TM) |
| yara* | |
| (4-isopropylcyclohexadienyl)ethyl formate | |

Examples of fragrance materials which lie within category B, but have Kovats index above 1600 and so are outside category B, are listed in the following table:

| Within category B but outside category B' | |
|---|---|
| amyl cinnamate | |
| amyl cinnamic aldehyde | |
| amyl cinnamic aldehyde dimethyl acetal | |
| cinnamyl cinnamate | |
| 1,2,3,5,6,7,8,8a,-octathyro-1,2,8,8-tetramethyl-2-acetyl naphthalene | (iso E super (TM) |
| cyclo-1,13-ethylenedioxytridecan-1,13-dione | (ethylene brassylate) |
| cyclopentadecanolide | (Exaltolide, TM) |
| hexyl cinnamic aldehyde | |
| 1,3,4,6,7,8-hexahydro-4,6,6,7,8,8-hexamethylcyclopenta[g]-2-benzopyran | (Galaxolide, TM) |
| geranyl phenyl acetate | |
| 6-acetyl-1-isopropyl-2,3,3,5-tetramethylindane | (Traseolide, TM) |
| 1,1,2,4,4,7-hexamethyl-6-acetyl-1,2,3,4-tetrahydronaphthalene | (Tonalid, TM) |

As indicated above, it is particularly preferred to utilise a perfume composition which has deodorant properties. Preferably, the perfume is a deodorant perfume giving a Malodour Reduction Value of at least 0.5, preferably at least 0.9, in the Malodour Reduction Value test described below and which is an adaptation of the test described in EP-A-147191 and corresponding U.S. Pat. No. 4,663,068.

The Malodour Reduction Value Test

In this test, the Malodour Reduction Value of a deodorant perfume is measured by assessing its effectiveness, when applied to fabric, in reducing body malodour when the fabric so treated is placed in contact with the axillae (armpits) of a panel of human subjects, and held there for a standard period of time. From subsequent olfactory evaluation by trained assessors, a Malodour Reduction Value can be calculated so giving a measure of the effectiveness as a deodorant of the perfume under test.

Stage 1 is preparation of the perfume treated fabric. A test fabric is subjected to a textile finishing which applies perfume to the fabric at a predetermined percentage of perfume composition, by weight of the cloth. A control fabric is given similar treatment, with or without perfume, depending on the purpose of the test. Depending on the purpose of the test, the fabrics may subsequently be washed and dried.

The test and control fabrics are cut into 20 cm×20 cm squares for testing.

Stage 2 is the carrying out of the test. A team of three Caucasian female assessors of minimum age 20 years is selected to carry out olfactory evaluation on the basis that each is able to rank correctly the odour levels of the series of standard aqueous solutions of isovaleric acid listed below, and each is able to assign a numerical score, corresponding to the odour intensity of one of these solutions, to the body malodour of a shirt insert after has been worn in the axillary region by a male subject for a standard period of time.

A panel of 40 human subjects for use in the test is assembled from Caucasian male subjects of age within the range of from 20 to 55 years. By screening, subjects are chosen who develop axillary body malodour that is not unusually strong and who do not develop a stronger body malodour in one axilla compared with the other. Subjects who develop unusually strong body malodour, for example due to a diet including curry or garlic, are not selected for the panel.

For two weeks before the start of the test, the panel subjects are assigned an unperfumed, non-deodorant soap bar for exclusive use when washing and are denied the use of any other type of deodorant or antiperspirant. At the end of this period, the 40 subjects are randomly divided into two groups of 20.

The "test" and "control" fabric pieces are then tacked into 40 clean cotton or polyester cotton shirts in the underarm region in such a manner that in 20 shirts, the control fabric pieces are attached inside the left underarm region, and the test fabric pieces are attached in the right underarm region. For the remaining 20 shirts, the placing of control and test pieces of fabric is reversed.

The shirts carrying the tacked-in fabric inserts are then worn by the 40 panel members for a period of 5 hours, during which time each panellist performs his normal work function without unnecessary exercise.

After this five hour period, the shirts are removed and the inserts detached and placed in polyethylene pouches prior to assessment by the trained panel of assessors.

The malodour intensity of each fabric insert is evaluated by all three assessors who, operating without knowledge of which inserts are "test" and in which are "control" and, without knowing the scores assigned by their fellow assessors, sniff each fabric piece and assign to it a score corresponding to the is strength of the odour on a scale from 0 to 5, with 0 representing no odour and 5 representing very strong odour.

Standard aqueous solutions of isovaleric acid which correspond to each of the scores 1, 2, 3, 4 and 5 are provided for reference to assist the assessors in the malodour evaluation. These are shown below:

| SCORE | ODOUR LEVEL | CONCENTRATION OF AQUEOUS ISOVALERIC ACID (ML/L) |
|---|---|---|
| 0 | NO ODOUR | 0 |
| 1 | SLIGHT | 0.013 |
| 2 | DEFINITE | 0.053 |
| 3 | MODERATE | 0.22 |
| 4 | STRONG | 0.87 |
| 5 | VERY STRONG | 3.57 |

The scores recorded by each assessor for each fabric piece are averaged. The average score of the "test" fabric pieces is deducted from the average score of the "untreated" control fabric pieces to give a Malodour Reduction Value.

As a check that the selection of panel subjects is satisfactory for operation of the test, the average score with unperfumed fabric pieces should be between 2.5 and 3.0.

Preferred deodorant perfumes are those which have a Malodour Reduction Value of at least 0.50, or 0.70, or 1.00. The higher the minimum value, the more effective is the perfume as a deodorant as recorded by the assessors in the Malodour Reduction Value Test. It has also been noted that consumers, who are not trained assessors, can detect by self-assessment a noticeable reduction in malodour on soiled fabric such as shirts and underclothes where the Malodour Reduction Value is at least 0.30, so the higher the Malodour Reduction Value above this figure, the more noticeable is the deodorant effect.

Selection of a combination of fragrance materials to give a deodorant effect is explained in patents such as U.S. Pat. No. 4,306,79 referred to earlier. Further systems of selection are given in U.S. Pat. No. 5,482,635 and U.S. Pat. No. 5,554,588 also mentioned above.

Such selections can be carried out using materials with preferred values of partition coefficient and Kovats index as discussed above.

U.S. Pat. No. 5,501,805 describes perfume compositions made from a combination of fragrance materials, where the composition is a deodorant perfume yet has a relatively low odour. Such "low-odour" deodorant perfumes may be used in the present invention.

When this test is used to assess the deodorant effectiveness of a perfume composition, applied to fabric in accordance with this invention, the test fabric is a blend of 95% by weight cotton and 5% by weight spandex fibres. The control fabric is 100% cotton. The test and control fibres are selected to be similar in other respects, in particular to have the same weight per unit area.

The test fabric is subjected to treatment with a fabric finishing liquor, containing perfume, so as to apply 0.5% of the perfume, by weight of the fabric. The control fabric is treated similarly, but without perfume.

The test and control fabrics are not subsequently washed before testing.

However, this test procedure can be operated in other ways. To demonstrate the higher deposition of perfume on spandex fibres, the control and test fabrics are both treated with the same fabric finishing liquor containing perfume. To isolate the deodorant effect of the perfume, the test and control fabrics can be the same, but no perfume is present in the liquor used to treat the control fabric.

EXAMPLE 1

This model experiment demonstrates perfume deposition on spandex fibres. A mixture of perfume ingredients was prepared and added to an unperfumed, but otherwise conventional, laundry detergent powder, to provide a perfume concentration of 0.5% by weight.

The perfumed powder was used to wash test cloths which had not previously been treated with any perfume. These were either all cotton, or 95% cotton with 5% spandex. After washing, the cloths were rinsed and then line dried overnight.

The perfume was extracted from the dry cloths with organic solvent, and the content of the perfume ingredients in the solvent extracts was determined by gas chromatography. If the concentration of an ingredient extracted from the spandex-containing cloth was greater than from the all-cotton cloth by a factor of 5 to 20, the result was coded as a medium enhancement (M). If the concentration was greater by 20 or more, it was coded high(H) and if less than 5 or not measurable, it was coded(L). The results obtained were as follows:

| Ingredient | K* | logP** | Enhancement | Category |
|---|---|---|---|---|
| Boisambrene Forte | 1714 | 5.5 | M | B |
| benzyl acetone | 1206 | 2.0 | M | — |
| citronellol | 1209 | 3.6 | H | A' |
| 2,6-dimethyl-heptan-2-ol | 975 | 2.9 | L | — |
| jasmacyclene | 1394 | 2.9 | H | B' |
| methyl salicylate | 1167 | 2.3 | L | — |
| 2-phenylethanol | 1087 | 1.4 | L | — |
| terpinyl acetate | 1331 | 4.0 | H | B' |
| tetrahydrogeraniol | 1180 | 3.6 | H | A' |
| tetrahydrolinalol | 1083 | 3.5 | H | A' |
| Tonalid | 1840 | 6.4 | M | B |
| yara | 1416 | 3.2 | H | B' |

*Measured on OV-1 polydimethylsiloxane (Ohio Valley) as stationary phase using capiliary gc
**Measured or estimated using 'logP' software from ACD Inc.

EXAMPLE 2

Cloth composed of 90% cotton, 10% spandex, was treated in a fabric finishing step, using conventional equipment. Other cloth, consisting of cotton only, was treated in the same way. In both cases, the fabric finishing treatment was carried out for a period of 20 minutes, using an MCS jet machine (Urgano, Italy). The finishing liquors were applied applied at a liquor to cloth ratio of 20:1, at 40° C. with a pH of 5.5. These liquors all contained Ceranine HCS (a finishing agent made by Sandoz) at a concentration such that this agent was applied to fabric at 1% by weight of the fabric.

The treatment liquors also contained perfume at varying concentrations, so that this was applied to the fabric at concentrations of 0.01%, 0.1% and 1% by weight of the fabric. Liquor without perfume was used to provide a control.

The perfume was used, designated "perfume U" contained 33.5% (by weight of the perfume composition) of fragrance materials in category A above, all of which had Kovats indices of 1050 to 1600 and therefore all fell within category A'. The perfume also contained 41.1% (by weight of the perfume composition) of materials in category B. These were made up from 26.7% with Kovats index over 1600 and 14.4% with Kovats index of 1300 to 1600, so as to fall within category B'.

The cloths were then washed repeatedly, using a commercial detergent powder which included a different perfume. The washes were carried out using a Miele washing machine on its "Quickwash" programme at 40° C. 110 gm of detergent powder was used for each wash. The fabric was rinsed three times after each wash and tumble dried.

The dried cloths were examined by a panel of in expert assessors of perfume intensity. This was to determine the intensity of perfume on the fabric, but not its deodorant property. The results obtained were as follows:

| | Odour Evaluation Scores | | | | | |
|---|---|---|---|---|---|---|
| | 100 cotton | | | 90% cotton and 10% spandex | | |
| Washes: | 1 | 3 | 5 | 1 | 3 | 5 |
| Perfume U | | | | | | |
| 0% | 2.0 | 2.4 | 2.8 | 4.0 | 4.4 | 4.6 |
| 1.0% | 6.4 | 3.6 | <3 | 16.0 | 14.0 | 12.8 |
| 0.1% | 3.6 | <3 | <3 | 10.4 | 9.7 | 9.0 |
| 0.01% | 3.2 | <3 | <3 | 8.8 | 8.0 | 7.2 |

It can be seen that the cloths which were not perfumed in the finishing treatment took up perfume in the first wash and this perfume built up slowly in subsequent washes. The quantity of perfume taken up was greater on the cloth which included spandex fibres.

The cloths containing spandex fibres which were perfumed during the finishing treatment had a much higher level of perfume on them after one wash than the 100% cotton cloths. Even after five washes, the intensity of perfume on them exceeded the intensity of perfume on the 100% cotton cloths after one wash, and on the cloths which had not been perfumed prior to the first wash. Thus the spandex fibres were providing enhanced retention of perfume as well as enhanced deposition.

The 100% cotton cloths which had been perfumed during the finishing treatment were assessed again after 3 and 5 washes. The results showed that the level of intensity of the perfume was less than that observed after 1 wash but also showed that the olfactive differences between perfume U used in the finishing treatment and the perfume present in the washing powder was confusing the panellists.

EXAMPLE 3

Two deodorant perfumes were used in treatment of cloths by a finishing process as in Example 2.

Perfume L contained materials in the above categories as follows:

Category A: 30 wt % (all with Kovats index above 1600)

Category B: 68.5 wt % (13% with Kovats index 1300–1600 and therefore within category B', and 55.5 wt % with Kovats index above 1600).

Perfume M contained materials in the above categories as follows:

Category A: 24.9 wt % (16.3 wt % with Kovats index 1050–1600 and therefore within category A', and 8.6 wt % with Kovats index above 1600)

Category B: 55.3 wt % (8.6 wt % with Kovats index 1300–1600 and therefore within category B', and 46.7 wt % with Kovats index above 1600).

The test cloths were: 100% cotton, 90% cotton with 10% spandex, 95% cotton with 5% spandex, 100% nylon and 82% nylon with 18% spandex. Perfume was used at a concentration of 0.5% based on the weight of the fabric. The treated cloths were tested for Malodour reduction in the test described earlier. The control cloths were 100% cotton, which had been subjected to the same finishing treatment, but without perfume in that finishing treatment. The results are set out in the following tables, which show substantial enhancements of malodour inhibition when fabrics containing spandex fibres were used.

Test 1:

| Fabric | | perfume M (% by weight | | | Malodour reduction |
|---|---|---|---|---|---|
| other fibre | spandex | of fabric) | Malodour score | Maldour reduction | as % of control |
| 90% cotton | 10% | 0.5% | 1.19 | 1.46 | 55% |
| 100% cotton | 0 | 0.5% | 1.92 | 0.73 | 27.4% |
| 82% nylon | 18% | 0.5% | 1.00 | 1.65 | 62.1% |
| 100% nylon | 0 | 0.5% | 1.97 | 0.68 | 25.5% |
| 100% cotton (control) | 0 | 0 | 2.65 | | |

Notes: % malodour reduction calculated as 100% x(control score-sample score)/control score Statistical calculation showed that a difference in malodour reduction of 6.9% was significant at 95% level of confidence.

Test 2:

| Fabric | | perfume M (% by weight | | | Malodour reduction |
|---|---|---|---|---|---|
| other fibre | spandex | of fabric) | Malodour score | Maldour reduction | as % of control |
| 95% cotton | 5% | 0.5% L | 1.15 | 1.22 | 51.5% |
| 95% cotton | 5% | 0.5% M | 1.29 | 1.08 | 45.6% |
| 100% cotton (control) | 0 | 0 | 2.37 | | |

Note: Statistical calculation showed that a difference in malodour reduction of 6.3% was significant at 95% level of confidence.

In test 1, malodour scores on 100% cotton fabric, with and without perfume, demonstrate a malodour reduction value of 0.73 attributable to the perfume. A similar malodour reduction value was observed when the test cloth was 100% nylon.

When spandex fibre was incorporated, the malodour reduction increased greatly, showing that increased deposition of perfume on spandex fibres compared with other fibres also provides an increased deodorant efficiency.

In test 2, similar high values of malodour reduction were obtained when either perfume L or perfume M was used, in test fabrics with 5% by weight spandex fibres.

What is claimed is:

1. A spandex fiber having fragrance materials deposited on the spandex fiber from a solution wherein the fragrance materials are selected from:

Category A) hydroxylic materials which are alcohols, phenols or salicylates, with an octanol/water partition coefficient (P) whose common logarithm (log10P) is 2.5 or greater, and a gas chromatographic Kovats index (as determined on polydimethylsiloxane as non-polar stationary phase) of at least 1050, and Category B) esters ethers, nitrites, ketones or aldehydes, with an octanol/water partition coefficient (P) whose common logarithm (log10P) is 2.5 or greater, and a gas chromatographic Kovats index (as determined on polydimethylsiloxane as non-polar station phase) of at least 1300.

2. A textile which comprises spandex and other fibers and which has fragrance materials preferentially deposited on the spandex fibers from a solution wherein the fragrance materials are selected from:

Category A) hydroxylic materials which are alcohols, phenols or salicylates, with an octanol/water partition coefficient (P) whose common logarithm (log10P) is 2.5 or greater, and a gas chromatographic Kovats index (as determined on polydimethylsiloxane as non-polar stationary phase) of at least 1050, and Category B) esters ethers, nitrites, ketones or aldehydes, with an octanol/water partition coefficient (P) whose common logarithm (log10P) is 2.5 or greater, and a gas chromatographic Kovats index (as determined on polydimethylsiloxane as non-polar station phase) of at least 1300.

3. A textile which is yarn or textile goods that have never been worn as garments and that contain spandex, comprising contacting the textile with a solution containing a perfume composition which is a mixture of fragrance materials, so that fragrance materials are deposited on the textile, wherein the perfume composition contains at least 50%, by weight of the perfume composition, of fragrance materials selected from Category A) hydroxylic materials which are alcohols, phenols or salicylates, with an octanol/water partition coefficient (P) whose common logarithm ($log_{10}P$) is 2.5 or greater, and a gas chromatographic Kovats index (as determined on polydimethylsiloxane as non-polar stationary phase) of at least 1050, and Category B) esters, ethers, nitriles, ketones or aldehydes, with an octanol/water partition coefficient (P) whose common logarithm ($log_{10}P$) is 2.5 or greater, and a gas chromatographic Kovats index (as determined on polydimethylsiloxane as non-polar stationary phase) of at least 1300.

4. A textile according to claim 3 which contains from 0.5 to 50% spandex fibers and the amount of fragrance materials deposited thereon is from 0.001% to 1% by weight of the textile.

5. A method of treating textile which is yarn or textile goods that have never been worn as garments and that contain spandex, comprising contacting the textile with a solution containing a perfume composition which is a mixture of fragrance materials, so that fragrance materials are deposited on the textile, wherein the perfume composition contains at least 50%, by weight of the perfume composition, of fragrance materials selected from Category A) hydroxylic materials which are alcohols, phenols or salicylates, with an octanol/water partition coefficient (P) whose common logarithm ($log_{10}P$) is 2.5 or greater, and a gas chromatographic Kovats index (as determined on polydimethylsiloxane as non-polar stationary phase) of at least 1050, and Category B) esters, ethers, nitrites, ketones or aldehydes, with an octanol/water partition coefficient (P) whose common logarithm ($log_{10}P$) is 2.5 or greater, and a gas chromatographic Kovats index (as determined on polydimethylsiloxane as non-polar stationary phase) of at least 1300.

6. A method according to claim 5 wherein the textile contains from 0.5 wt % to 50 wt % spandex fibers and the amount of fragrance materials deposited on the textile is from 0.001% to 1% by weight of the textile.

7. A method of treating a spandex fiber comprising contacting the fiber with a solution containing a perfume composition which is a mixture of fragrance materials, so that fragrance materials are deposited on the spandex fiber, wherein the perfume composition contains at least 50%, by weight of the perfume composition, of fragrance materials selected from Category A) hydroxylic materials which are alcohols, phenols or salicylates, with an octanol/water partition coefficient (P) whose common logarithm ($log_{10}P$) is 2.5 or greater, and a gas chromatographic Kovats index (as determined on polydimethylsiloxane as non-polar stationary phase) of at least 1050, and Category B) esters, ethers, nitriles, ketones or aldehydes, with an octanol/water partition coefficient (P) whose common logarithm ($log_{10}P$) is 2.5 or greater, and a gas chromatographic Kovats index (as determined on polydimethylsiloxane as non-polar stationary phase) of at least 1300.

8. A method according to claim 5 or claim 7 wherein the perfume composition contains at least 10%, by weight of the perfume composition, of fragrance materials selected from:

Category A') hydroxylic materials which are alcohols, phenols or salicylates, with an octanol/water partition coefficient (P) whose common logarithm ($log_{10}P$) is 2.5 or greater, and a gas chromatographic Kovats index (as determined on polydimethylsiloxane as non-polar stationary phase) lying within the range 1050 to 1600, and Category B') esters, ethers, nitriles, ketones or aldehydes, with an octanol/water partition coefficient (P) whose common logarithm ($log_{10}P$) is 2.5 or greater, and a gas chromatographic Kovats index (as determined on polydimethylsiloxane as non-polar stationary phase) lying within the range 1300 to 1600.

9. A method according to claim 5 or claim 7 wherein the perfume composition contains at least 70%, by weight of the perfume composition, of fragrance materials that are selected from categories A and B, which materials include at least 25% by weight of the perfume composition, of fragrance materials from the categories A' and B' defined in claim 8.

10. A method according to claim 9 wherein the perfume composition contains at least 80%, by weight of the perfume composition, of fragrance materials selected from categories A and B, which materials include at least 40%, by weight of the perfume composition, from categories A' and B'.

11. The method of claim 5, wherein the fabric is contacted with the perfume composition in a fabric finishing step.

* * * * *